(12) United States Patent
Hiraki et al.

(10) Patent No.: US 7,081,254 B1
(45) Date of Patent: Jul. 25, 2006

(54) SKIN PREPARATIONS FOR EXTERNAL USE

(75) Inventors: Yoshio Hiraki, Tokyo (JP); Satoshi Yoshikawa, Tokyo (JP); Takashi Kinoshita, Tokyo (JP); Tatsutoshi Shiraishi, Tokyo (JP); Toshiro Sone, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/913,721

(22) PCT Filed: Feb. 16, 2000

(86) PCT No.: PCT/JP00/00856

§ 371 (c)(1),
(2), (4) Date: Aug. 17, 2001

(87) PCT Pub. No.: WO00/48566

PCT Pub. Date: Aug. 24, 2000

(30) Foreign Application Priority Data

Feb. 17, 1999 (JP) ................... 11-038392

(51) Int. Cl.
A61K 9/127 (2006.01)
A61K 6/00 (2006.01)

(52) U.S. Cl. .............. 424/450; 424/401; 514/415
(58) Field of Classification Search ............. 424/401, 424/405; 514/932, 938
See application file for complete search history.

(56) References Cited

U.S. PATENT DOCUMENTS

| 4,603,146 A | 7/1986 | Kligman |
| 4,877,805 A | 10/1989 | Kligman |
| 4,888,342 A | 12/1989 | Kligman |
| 5,013,497 A * | 5/1991 | Yiournas et al. ............. 264/4.1 |
| 5,034,228 A | 7/1991 | Meybeck et al. |
| 5,260,065 A * | 11/1993 | Mathur et al. .............. 424/450 |
| 5,643,587 A | 7/1997 | Scancarella et al. |

FOREIGN PATENT DOCUMENTS

| EP | 0721775 A2 | 7/1992 |
| EP | 0 834 301 | 4/1998 |
| JP | 64-500355 | 2/1989 |
| JP | 3-118312 | 5/1991 |
| JP | 4-338311 | 11/1992 |
| JP | 2606761 | 11/1992 |
| JP | 7-118134 | 5/1995 |
| JP | 7-165530 | 6/1995 |
| JP | 8-225439 | 9/1996 |
| JP | 9-175931 | 7/1997 |
| JP | 10-29929 | 2/1998 |
| WO | WO 96/31194 | 10/1996 |
| WO | WO 98/14167 | 4/1998 |

* cited by examiner

Primary Examiner—Sreeni Padmanabhan
Assistant Examiner—Gina C. Yu
(74) Attorney, Agent, or Firm—Oblon, Spivak, McClelland, Maier & Neustadt, P.C.

(57) ABSTRACT

The invention relates to a skin preparation for external use, which contains a lamellar structure containing a fatty acid monoglyceride as a main component, and vitamin A or a derivative thereof. The skin preparation for external use has high effects of improving skin roughness and suppressing wrinkling, etc., shows neither any offensive smell nor stickiness, and exhibits controlled foaming upon the production thereof.

7 Claims, No Drawings

SKIN PREPARATIONS FOR EXTERNAL USE

TECHNICAL FIELD

The present invention relates to a skin preparation for external use (hereinafter may also be referred to as "external skin care composition") which has a high moisturizing effect, high effects of relieving or improving skin roughness and suppressing wrinkling, etc., shows neither any offensive smell nor stickiness, gives users a dry feel upon use, and exhibits controlled foaming upon production thereof and excellent stability.

BACKGROUND ART

The skin is delicately affected by aging, and external environments such as temperature, humidity and ultraviolet rays, etc. Therefore, the decrement of various functions of the skin, and aging of the skin are brought about, and various troubles such as wrinkling and skin roughness occur. In order to improve these cutaneous troubles, it has been attempted to incorporate various components having a skin roughness-improving effect and an anti-aging effect, such as synthetic or natural moisturizing components, natural extracts such as sesame oil, rutin sugar derivatives, proteins such as sericin, and α-hydroxy acids into external skin care compositions such as cosmetic compositions.

For example, polyhydric alcohols such as glycerol and propylene glycol; saccharides such as sorbitol and maltitol; amino acids; polymeric substances such as hyaluronic acid and chondroitin sulfate; etc. are known as the moisturizing components. However, the use of these moisturizing agents involves a problem that a sticky feel is given users.

The present applicant found and discloses that a lamellar structure comprising a fatty acid monoglyceride as a main component has a high moisturizing effect (Japanese Patent Registration No. 2606761). However, occurrence of foaming is unavoidable in the production of this lamellar structure, which becomes a problem from the viewpoint of production efficiency. In addition, there may be offered a problem that a part of the lamellar structure is destroyed according to conditions of storage.

Japanese Patent Application Laid-Open No. 500355/1989 through PCT route discloses a method for preventing or improving changes or damages of the skin due to skin aging and/or exposure to sunlight by incorporating vitamin A or a derivative thereof. However, vitamin A is insufficient in effects of improving skin roughness and suppressing wrinkling and also involves a problem that it forms the cause of offensive smell and stickiness.

It is therefore an object of the present invention to provide a skin preparation for external use which has high effects of improving skin roughness and suppressing wrinkling, etc., shows neither any offensive smell nor stickiness, and exhibits controlled foaming upon production thereof.

DISCLOSURE OF THE INVENTION

The present inventors have carried out an extensive investigation with a view toward solving the above-described problems. As a result, it has been found that when a lamellar structure comprising a fatty acid monoglyceride as a main component and vitamin A or a derivative thereof are used in combination, the effects of vitamin A on improvement in skin roughness, suppression of wrinkling, etc. are enhanced, and the resulting composition gives users a dry feel upon use and that when an oil phase mixture containing a fatty acid monoglyceride and vitamin A is prepared and a lamellar structure is then prepared from the oil phase mixture, higher effects of improving skin roughness and suppressing wrinkling are achieved, and the smell of vitamin A, foaming upon the production of the lamellar structure can be suppressed, and moreover shelf stability of the resulting external skin care composition is also improved, thus leading to completion of the present invention.

Thus, the present invention provides an external skin care composition comprising a lamellar structure containing a fatty acid monoglyceride as a main component, and vitamin A or a derivative thereof.

BEST MODE FOR CARRYING OUT THE INVENTION

Examples of the fatty acid monoglyceride used in the present invention include monoglycerides of saturated or unsaturated fatty acids having 8 to 18 carbon atoms. Among these, myristic acid monoglyceride, palmitic acid monoglyceride and stearic acid monoglyceride are preferred. These monoglycerides may be used either singly or in any combination thereof.

The lamellar structure used in the present invention contains the fatty acid monoglyceride as a main component. As constitutive components of the lamellar structure, other components may be used in addition to the fatty acid monoglyceride. Such constitutive components include cholesterol and the like. The incorporation of cholesterol is particularly preferred for the purpose of improving the stability of the lamellar structure. The amount of cholesterol added is preferably 0.01 to 1 part by weight, particularly 0.05 to 0.40 parts by weight per part by weight of the fatty acid monoglyceride.

In the present invention, the lamellar structure is prepared by using the fatty acid monoglyceride or an oil phase mixture containing the fatty acid monoglyceride as a raw material. For example, the fatty acid monoglyceride or the oil phase mixture containing the fatty acid monoglyceride is heated to melt and mix it into a state of a liquid crystal, and a water phase kept at substantially the same temperature is then added to the oil phase to disperse the oil phase in the water phase by physically stirring the mixture, whereby a dispersion of the lamellar structure used in the present invention can be prepared. The heating temperature is preferably 45 to 100° C., more preferably 45 to 80° C., particularly 50 to 70° C. The physical stirring in this process is preferably conducted by using an atomizing device such as an ultrasonic emulsifier, high-pressure, homogeneously dispersing device, nanomizer, homomixer, homogenizer, colloid mill or high-speed stirrer. As an alternative process, the lamellar structure used in the present invention may also be prepared by dissolving the fatty acid monoglyceride or the oil phase mixture containing the fatty acid monoglyceride in a solvent such as dichloromethane, chloroform or acetone, distilling off the solvent in a rotating container to deposit a lipid layer, and then adding and mixing water or a proper aqueous solution to and with the lipid. Between both preparation processes, the former process is preferred from the viewpoint of industrial production.

No particular limitation is imposed on the form of the lamellar structure. However, the same form as a vesicle, i.e., a closed lamellar structure is preferred. Such a closed lamellar structure is preferably a multi-lamellar structure, not a unilamellar structure.

No particular limitation is imposed on the vitamin A or the derivative thereof (hereinafter referred to as "vitamin A" merely) used in the present invention, and any of retinol, retinal of the aldehyde type, retinoic acid of the carboxylic acid type, and esters such as retinol acetate and retinol palmitate may be preferably used. Besides, vitamin A precursors such as β-carotin and decomposed products of vitamin A, such as hydroretinol, retroretinol and isoanhydroretinol may also be used. Among these, retinol palmitate, retinol, retinoic acid and retinol acetate preferred from the viewpoint of effects of improving skin roughness and suppressing wrinkling, with retinol palmitate being particularly preferred. These compounds may be used either singly or in any combination thereof.

With respect of contents of the fatty acid monoglyceride and vitamin A in the external skin care composition according to the present invention, the content of the fatty acid monoglyceride is preferably 0.1 to 25% by weight, particularly 0.5 to 10% by weight from the viewpoint of stability of the lamellar structure, while the content of the vitamin A is preferably 0.001 to 2% by weight, particularly 0.01 to 0.3% by weight from the viewpoints of the effects of improving skin roughness and suppressing wrinkling, cost and workability.

The external skin care composition according to the present invention may also be prepared by preparing the lamellar structure and then incorporating it together with the vitamin A and other components into the external skin care composition. However, it is preferable to first prepare an oil phase mixture containing the fatty acid monoglyceride and vitamin A, prepare the lamellar structure from this oil phase mixture according to the process described above and then incorporate it together with other components into the external skin care composition. The effects of the vitamin A on improvement in skin roughness and suppression of wrinkling are enhanced by any process. However, these effects are particularly enhanced by preparing the lamellar structure from the mixture of the fatty acid monoglyceride and vitamin A. According to this process, the offensive smell caused by the vitamin A can be suppressed, foaming occurred upon the production of the lamellar structure can also be suppressed, and moreover the stability of the lamellar structure is enhanced, thereby providing an external skin care composition excellent in shelf stability.

Viewing from the state of the vitamin A in the external skin care composition, the vitamin A is preferably contained within or covered with the lamellar structure from the above-described point of view.

When the lamellar structure is prepared from the oil phase mixture containing the fatty acid monoglyceride and vitamin A as described above, the mixing ratio of the fatty acid monoglyceride to the vitamin A is preferably 2 to 100 parts by weight, particularly 5 to 50 parts by weight for the fatty acid monoglyceride per part by weight of the vitamin A from the viewpoints of the degree of suppression of foaming, stability to storage, etc. More specifically, if the content of the fatty acid monoglyceride is higher than this range, the effect of suppressing foaming upon the production is lessened. If the content is lower than this range on the other hand, the stability of the lamellar structure is deteriorated.

The external skin care compositions according to the present invention obtained in such a manner can be used as cosmetics, drugs, quasi-drugs, medicines for external use, etc. Among these, they are preferably used as cosmetics for improving skin roughness, suppressing wrinkling or preventing aging. No particular limitation is imposed on the form of such cosmetics, and they may be used in various forms, for example, toilet waters, emulsified compositions, moisturizing creams, cleansing creams, massaging creams, face cleansing creams, packs, beauty lotions, hair cosmetics, mouth cosmetics, etc.

Into the external skin care compositions according to the present invention, may be incorporated publicly known cosmetic components and drug components, for example, water, alcohols, surfactants, preservatives, perfume bases, coloring matter, various kinds of medicinally-effective components, etc. so far as no detrimental influence is thereby imposed on the effects of the present invention.

EXAMPLES

The present invention will hereinafter be described in more detail by the following examples. However, the present invention is not limited to these examples.

Test Example 1

Wrinkling-Suppressing Test

An influence of the following samples on the skin roughness and wrinkling of hairless mice by exposure to an ultraviolet ray.

(Preparation of Sample)

Invention Product 1:

(1) A phase: After a fatty acid monoglyceride (d) and cholesterol (e) of 1A as shown in Table 1 were heated at 80° C. and mixed into a solution, and the resultant solution was cooled to 65° C., the solution was added to a solution with calcium chloride (a) and methylparaben (b) dissolved in purified water (c) at 60° C., and the resultant mixture was stirred and mixed by a homomixer to obtain a dispersion of a lamellar structure.

(2) B phase: Calcium chloride (a), methylparaben (b) and purified water (c) of 1B as shown in Table 1 were heated at 80° C. and mixed into a solution. On the other hand, retinol palmitate (f), liquid paraffin (g) and surfactants (h, i) were also heated at 80° C. and mixed into a solution. Both solutions were stirred and mixed with each other and then cooled to obtain an emulsion.

(3) The A phase and B phase were stirred and mixed at room temperature to obtain an emulsified composition (Invention Product 1).

Invention Product 2:

(1) A phase: After a fatty acid monoglyceride (d), cholesterol (e) and retinol palmitate (f) of 2A as shown in Table 1 were heated at 80° C. and mixed into a solution, and the resultant solution was cooled to 65° C., the solution was added to a solution with calcium chloride (a) and methylparaben (b) dissolved in purified water (c) at 60° C., and the resultant mixture was stirred and mixed by a homomixer to obtain a dispersion of a lamellar structure.

(2) B phase: Calcium chloride (a), methylparaben (b) and purified water (c) of 1B as shown in Table 1 were heated at 80° C. and mixed into a solution. On the other hand, liquid paraffin (g) and surfactants (h, i) were also heated at 80° C. and mixed into a solution. Both solutions were stirred and mixed with each other and then cooled to obtain an emulsion.

(3) The A phase and B phase were stirred and mixed at room temperature to obtain an emulsified composition (Invention Product 2).

Comparative Product 1:

Calcium chloride (a), methylparaben (b) and purified water (c) of 3A as shown in Table 1 were heated at 80° C. and mixed into a solution. On the other hand, retinol palmitate (f), liquid paraffin (g) and surfactants (h, i) were also heated at 80° C. and mixed into a solution. Both solutions were stirred and mixed with each other and then cooled to obtain an emulsified composition (Comparative Product 1).

TABLE 1

|  | Invention product 1 | | Invention product 2 | | Comparative product 1 |
| --- | --- | --- | --- | --- | --- |
|  | 1A (lamella) | 1B (emulsion) | 2A (lamella) | 2B (emulsion) | 3B (emulsion) |
| a. Calcium chloride | 0.05 | 0.05 | 0.05 | 0.05 | 0.1 |
| b. Methylparaben | 0.05 | 0.05 | 0.05 | 0.05 | 0.1 |
| c. Purified water | 43.5 | 34.9 | 42.4 | 35.9 | 84.8 |
| d. Poem s-100[1] | 5.0 | — | 5.0 | — | — |
| e. Cholesterol | 1.5 | — | 1.5 | — | — |
| f. Retinol palmitate | — | 1.0 | 1.0 | — | 1.0 |
| g. Liquid paraffin | — | 10.0 | — | 10.0 | 10.0 |
| h. TS-10[2] | — | 2.0 | — | 2.0 | 2.0 |
| i. SS-10[3] | — | 2.0 | — | 2.0 | 2.0 |

[1] A mixture of glyceryl monostearate and glyceryl monopalmitate (product of Riken Vitamin Co., Ltd.)
[2] Polyoxyethylene sorbitan monostearate (product of Nikko Chemicals Co., Ltd.)
[3] Sorbitan monostearate (product of Nikko Chemicals Co., Ltd.)

(Testing Method)

Forty hr-1 female hairless mice (aged 6 weeks) reared by freely giving ordinary solid feed and water in a thermo-hygrostatic breeding chamber controlled to 24±2° C. and 55±10% RH were divided into 4 groups each consisting of 10 mice and used.

These mice were exposed to an ultraviolet ray (UVB) 3 times a week under conditions of 40 to 160 mJ/cm$^2$. The samples shown in Table 1 was applied to mice of the respective groups every day in a dose of 10 µl/cm$^2$ to determine the degree of wrinkles after 14 days, 28 days and 42 days. Incidentally, the dose of the ultraviolet ray was increased stepwise within the above range.

The determination of wrinkles was conducted in the following manner. Namely, the shapes of the wrinkles were taken as replicas, and measurement of the wrinkles were computer-processed by means of an image analyzer to find a proportion (wrinkle percent) of an area of the wrinkles to the whole area. A relative value of each sample-applied group was calculated out from an average value of differences (increments of wrinkle percent) between the respective wrinkle percent after 14 days, 28 days and 42 days and the wrinkle percent before the exposure to the ultraviolet ray regarding a value as to a control group, to which no sample had been applied, as 100, thereby determining the average rate of wrinkling in each group.

(Result)

As a result, the external skin care compositions according to the present invention exhibited a higher effect of suppressing wrinkling than Comparative Product 1 (retinol palmitate alone) containing no lamellar structure, and the effect was particularly marked in Invention Product 2 in which the lamellar structure had been prepared together with retinol palmitate.

TABLE 2

| | Average value of increments of wrinkle percent after 14, 28 and 42 days | Average rate of wrinkling |
| --- | --- | --- |
| Control (no application) | 1.827 | 100 |
| Comparative Product 1 | 1.472 | 80.6 |
| Invention Product 1 | 1.386 | 75.9 |
| Invention Product 2 | 0.922 | 50.5 |

Test Example 2

Foaming Test and Shelf Stability Test

Dispersions of a lamellar structure were prepared in the same formulation and process as in Invention Product 2 of Test Example 1 except that the amounts of the vitamin A and fatty acid monoglyceride added were changed in various combinations, to confirm the foaming tendency upon the production thereof and stability to storage.

(Evaluation Method and Standard)

Foaming Tendency:

Foaming occurred upon the production was visually observed to judge the foaming tendency in accordance with the following standard:

0: Not foamed;

1: Somewhat foamed;

2: Foamed;

3: Considerably foamed.

Stability:

A state of deterioration of a vesicle after each dispersion of the lamellar structure was stored for 2 weeks or 4 weeks at 40° C. was observed through a microscope to judge the stability in accordance with the following standard:

0: Not deteriorated;

1: Srayly deteriorated;

2: Deteriorated;

3: Considerably deteriorated.

(Result)

As a result, the foaming tendency was suppressed in the case where the fatty acid monoglyceride was incorporated in a proportion of at most 100 times by weight, particularly at most 50 times by weight as much as the vitamin A (Table 3). The stability to storage was good in the case where the fatty acid monoglyceride was incorporated in a proportion of at least twice by weight, particularly at least 5 times by weight as much as the vitamin A (Table 4).

TABLE 3

Foaming tendency

| | | Concentration of fatty acid monoglyceride (% by weight) | | | | | | | |
|---|---|---|---|---|---|---|---|---|---|
| | | 0.1 | 0.2 | 0.5 | 1.0 | 5.0 | 10.0 | 20.0 | 25.0 | 30.0 |
| Concentration of vitamin A (% by weight) | 0 | 1 | 2 | 3 | 3 | 3 | 3 | 3 | 3 | 3 |
| | 0.005 | 1 | 2 | 3 | 3 | 3 | 3 | 3 | 3 | 3 |
| | 0.01 | 1 | 1 | 2 | 2 | 2 | 2 | 3 | 3 | 3 |
| | 0.05 | 0 | 1 | 1 | 1 | 2 | 2 | 2 | 2 | 2 |
| | 0.1 | 0 | 0 | 1 | 1 | 1 | 2 | 2 | 2 | 2 |
| | 0.2 | 0 | 0 | 1 | 1 | 1 | 1 | 2 | 2 | 2 |
| | 0.5 | 0 | 0 | 0 | 0 | 1 | 1 | 2 | 2 | 2 |
| | 1.0 | 0 | 0 | 0 | 0 | 1 | 1 | 1 | 2 | 2 |
| | 2.0 | 0 | 0 | 0 | 0 | 1 | 1 | 1 | 1 | 1 |
| | 5.0 | 0 | 0 | 0 | 0 | 0 | 0 | 1 | 1 | 1 |
| | 10.0 | 0 | 0 | 0 | 0 | 0 | 0 | 0 | 0 | 0 |
| | 20.0 | 0 | 0 | 0 | 0 | 0 | 0 | 0 | 0 | 0 |

TABLE 4

Stability

| | | Concentration of fatty acid monoglyceride (% by weight) | | | | | | | |
|---|---|---|---|---|---|---|---|---|---|
| | | 0.1 | 0.2 | 0.5 | 1.0 | 5.0 | 10.0 | 20.0 | 25.0 | 30.0 |
| Concentration of vitamin A (% by weight) | 0 | 0 | 0 | 0 | 0 | 0 | 0 | 0 | 0 | 1 |
| | 0.005 | 0 | 0 | 0 | 0 | 0 | 0 | 0 | 1 | 1 |
| | 0.01 | 1 | 0 | 0 | 0 | 0 | 0 | 0 | 1 | 1 |
| | 0.05 | 2 | 1 | 0 | 0 | 0 | 0 | 0 | 1 | 1 |
| | 0.1 | 3 | 2 | 1 | 0 | 0 | 0 | 0 | 1 | 1 |
| | 0.2 | 3 | 3 | 2 | 0 | 0 | 0 | 0 | 1 | 1 |
| | 0.5 | 3 | 3 | 3 | 1 | 0 | 0 | 0 | 1 | 1 |
| | 1.0 | 3 | 3 | 3 | 3 | 0 | 0 | 1 | 1 | 1 |
| | 2.0 | 3 | 3 | 3 | 3 | 1 | 1 | 1 | 1 | 1 |
| | 5.0 | 3 | 3 | 3 | 3 | 3 | 3 | 2 | 2 | 2 |
| | 10.0 | 3 | 3 | 3 | 3 | 3 | 3 | 3 | 3 | 3 |
| | 20.0 | 3 | 3 | 3 | 3 | 3 | 3 | 3 | 3 | 3 |

Test Example 3

Smell Suppressing Test

With respect to compositions prepared in accordance with the following preparation process, the degree of smell of the vitamin A, which is not very preferable as cosmetic, was got to be evaluated by 10 expert panelists in accordance with the following standard:

(Preparation Process)

a or b, and c and d in the formulation shown in Table 5 were mixed and headed to 80° C. into a solution. e and f were then mixed with g and heated to 60° C. into a solution. This solution was placed in a paddle agitator mixer equipped with a homomixer rotating at a high speed, and the above-prepared mixture of a or b, and c and d was added to the solution with stirring. After the resultant mixture was fully stirred at a high speed, the mixture was gradually cooled to room temperature.

(Evaluation Standard)
 0: Not smelled;
 1: Srayly smelled;
 2: Smelled;
 3: Considerably smelled.

(Result)

The results are shown as average values in Table 5.

TABLE 5

| | | | Invention Product 3 | Comparative Product 2 |
|---|---|---|---|---|
| Formulation (% by weight) | a | Soybean lecithin | — | 6.0 |
| | b | Glyceryl monopalmitate | 6.0 | — |
| | c | Cholesterol | 0.6 | 0.6 |
| | d | Retinol palmitate | 0.3 | 0.3 |
| | e | Sodium chloride | 0.1 | 0.1 |
| | f | Methylparaben | 0.1 | 0.1 |
| | g | Purified water | 92.9 | 92.9 |
| | | Smell right after preparation | 0.44 | 1.24 |
| | | Smell after 2 weeks at 40° C. | 0.92 | 2.18 |
| | | Smell after 4 weeks at 40° C. | 1.30 | 2.68 |

As apparent from Table 5, the lamellar structure prepared by the fatty acid monoglyceride in the invention product was markedly prevented from emitting smell from the vitamin A upon the preparation and after several days elapsed compared with the liposome preparation of the comparative product prepared by lecithin which is a soybean phospholipid.

Preparation Example

Their corresponding raw materials 1 to 8 shown in Table 6 were heated at 60 to 85° C. and mixed with one another. On the other hand, raw materials 9 to 12 and a part of purified water (13) were heated to 60° C. and mixed. To the mixture, was added the above-prepared mixed solution of the raw materials 1 to 8. The resulting mixtures were subjected to a mixing treatment by means of a homomixer for Composition 1, a high-pressure homogenizer for Composition 2, a high-speed stirrer for Composition 3 and an ultrasonic dispersing machine for Composition 4. Each of the mixtures was then mixed with raw materials 14 to 16 and the remainder of the purified water (13) under cooling, and the temperature thereof was returned to room temperature, thereby obtaining the respective compositions.

TABLE 6

| | | Composition | | | |
|---|---|---|---|---|---|
| | | 1 | 2 | 3 | 4 |
| 1 | Glyceryl monostearate | — | — | 2.0 | 5.0 |
| 2 | Glyceryl monopalmitate | 0.5 | 2.0 | — | 5.0 |
| 3 | Monostearyl glyceryl ether | 0.1 | — | 0.3 | — |
| 4 | Monopalmityl glyceryl ether | — | 0.5 | — | 3.0 |
| 5 | Cholesterol | 0.05 | 0.1 | 0.2 | 3.0 |
| 6 | Retinol palmitate | 0.1 | — | — | 2.0 |
| 7 | Retinol | — | 0.2 | — | — |
| 8 | Retinoic acid | — | — | 0.5 | — |
| 9 | Calcium chloride | 0.1 | 0.01 | 0.1 | 0.2 |
| 10 | Methylparaben | 0.1 | 0.1 | 0.1 | 0.2 |
| 11 | Glycerol | 1.0 | 1.0 | — | — |
| 12 | 1,3-Butylene glycol | — | — | 2.0 | 2.0 |
| 13 | Purified water | Balance | Balance | Balance | Balance |
| 14 | Polyvinyl pyrrolidone | 1.0 | 0.5 | — | — |
| 15 | Xanthan gum | — | — | 0.1 | — |
| 16 | Hyaluronic acid | — | — | — | 0.1 |

Example 1

Cosmetic Lotion

The following components were mixed in accordance with a method known per se in the art to prepare a cosmetic lotion.

| | |
|---|---|
| Composition 1 | 80 (wt. %) |
| Ethanol | 5 |
| Glycerol | 5 |
| 1,3-Butylene glycol | 5 |
| Methylparaben | 0.05 |
| Polyoxyethylene sorbitan monooleate | 0.5 |
| Carboxyvinyl polymer | 0.1 |
| Sodium hyaluronate | 0.01 |
| Perfume base | 0.05 |
| Purified water | Balance. |

Example 2

Cosmetic Milk

The following components were mixed in accordance with a method known per se in the art to prepare an cosmetic milk.

| | |
|---|---|
| Composition 2 | 50 (wt. %) |
| Stearic acid | 2 |
| Cetanol | 1 |
| Vaseline | 5 |
| Liquid paraffin | 10 |
| Polyoxyethylene sorbitan monooleate | 2 |
| Sorbitan monostearate | 2 |
| Butylparaben | 0.1 |
| 1,3-Butylene glycol | 5 |
| Carboxymethyl cellulose | 0.1 |
| Sodium hydroxide | 0.05 |
| Methylparaben | 0.1 |
| Perfume base | 0.05 |
| Purified water | Balance. |

Example 3

Cosmetic Cream

The following components were mixed in accordance with a method known per se in the art to prepare a cosmetic cream.

| | |
|---|---|
| Composition 4 | 50 (wt. %) |
| Stearic acid | 4 |
| Cetanol | 2 |
| Vaseline | 5 |
| Liquid paraffin | 10 |
| Jojoba oil | 5 |
| polyoxyethylene behenyl ether | 3 |
| Sorbitan monostearate | 3 |
| Butylparaben | 0.1 |
| 1,3-Butylene glycol | 2 |
| Sodium hydroxide | 0.05 |
| Methylparaben | 0.1 |
| Perfume base | 0.05 |
| Purified water | Balance. |

Example 4

Beauty Essence

The following components were mixed in accordance with a method known per se in the art to prepare a beauty essence.

| | |
|---|---|
| Composition 3 | 20 (wt. %) |
| Xanthan gum | 0.4 |
| Sodium hyaluronate | 0.05 |
| Ethanol | 5 |
| Glycerol | 2 |
| Paraben | 0.05 |
| Sorbitan polyoxyethylene monooleate | 0.5 |
| Perfume base | 0.05 |
| Purified water | Balance. |

Example 5

Face Washing Cream

The following components were mixed in accordance with a method known per se in the art to prepare a face washing cream.

| | |
|---|---|
| Composition 2 | 5 (wt. %) |
| Stearic acid | 10 |
| Palmitic acid | 10 |
| Myristic acid | 12 |
| Lauric acid | 4 |
| Oleyl alcohol | 1.5 |
| Butylparaben | 0.1 |
| Methylparaben | 0.1 |
| Perfume base | 0.5 |
| Glycerol | 18 |
| Potassium hydroxide | 6 |
| Purified water | Balance. |

Example 6

Pack

The following components were mixed in accordance with a method known per se in the art to prepare a pack.

| | |
|---|---|
| Composition 4 | 1 (wt. %) |
| Polyvinyl alcohol | 15 |
| Sodium carboxymethyl cellulose | 5 |
| Propylene glycol | 3 |
| Ethanol | 10 |
| Methylparaben | 0.1 |
| Purified water | Balance. |

Example 7

Cleansing Cream

The following components were mixed in accordance with a method known per se in the art to prepare a cleansing cream.

| | | |
|---|---|---|
| Composition 3 | 5 (wt. %) | |
| Paraffin | 10 | |
| Beeswax | 3 | |
| Vaseline | 15 | |
| Liquid paraffin | 41 | |
| Sorbitan sesquioleate | 4.2 | |
| Polyoxyethylene sorbitan monooleate (20 E.O.) | 0.8 | |
| Butylparaben | 0.1 | |
| Methylparaben | 0.1 | |
| Perfume base | 0.5 | |
| Purified water | Balance. | |

Example 8

Massaging Cream

Among the following components, raw materials 1 to 4 were heated at 85° C. and mixed, and raw materials 5 and 6, and a part of purified water 18 were heated to 60° C. and mixed. Both mixtures were mixed and the resultant mixture was treated by a homogenizer.

On the other hand, raw materials 7 to 14 were heated at 80° C. and mixed, and raw materials 15 and 16, and the remainder of purified water 18 were heated to 80° C. and mixed. Both mixtures were mixed, stirred and then cooled. A raw material 17 was added when this mixed solution (raw materials 7 to 16 and 18) was cooled to 50° C., and the resultant mixture was mixed with the above-prepared mixed solution (raw materials 1 to 6 and 18) at 40° C. to prepare a massaging cream.

| | | |
|---|---|---|
| 1 Glyceryl monostearate | 0.5 (wt. %) | |
| 2 Glyceryl monopalmitate | 0.5 | |
| 3 Monopalmityl glyceryl ether | 0.3 | |
| 4 Cholesterol | 0.3 | |
| 5 Calcium chloride | 0.02 | |
| 6 1,3-Butylene glycol | 0.02 | |
| 7 Paraffin | 4 | |
| 8 Microcrystalline wax | 6 | |
| 9 Beeswax | 6 | |
| 10 Vaseline | 14 | |
| 11 Liquid paraffin | 42.5 | |
| 12 Sorbitan sesquioleate | 3.7 | |
| 13 Polyoxyethylene sorbitan monooleate (20 E.O.) | 0.8 | |
| 14 Butylparaben | 0.1 | |
| 15 Methylparaben | 0.1 | |
| 16 Soap powder | 0.3 | |
| 17 Perfume base | 0.5 | |
| 18 Purified water | Balance. | |

INDUSTRIAL APPLICABILITY

The external skin care compositions according to the present invention have excellent effects of improving skin roughness and suppressing wrinkling, since a lamellar structure composed mainly of a fatty acid monoglyceride and a vitamin A are used in combination. Further, the effects of improving skin roughness and suppressing wrinkling are more enhanced, and moreover foaming occurred upon the production of the lamellar structure and smell of the vitamin A, which is not preferable as cosmetic, can be suppressed by preparing the lamellar structure from an oil phase mixture containing the fatty acid monoglyceride and vitamin A. In addition, the stability of the resulting external skin care composition can be improved.

The invention claimed is:

1. A skin preparation comprising a lamellar structure consisting of one or more fatty acid monoglyceride(s), and one or more of vitamin A and vitamin A precursor(s), derivative(s) and decomposed product(s) thereof, and cholesterol.

2. The skin preparation according to claim 1, wherein said one or more of vitamin A and vitamin A precursor(s), derivative(s) and decomposed product(s) thereof, and cholesterol is contained within or covered with the lamellar structure composed mainly of said one or more fatty acid monoglyceride(s).

3. The skin preparation according to any one of the claims 1 to 2, comprising a cosmetic composition.

4. The skin preparation according to claim 3, wherein said cosmetic composition is selected from the group consisting of a cosmetic lotion, a cosmetic milk, a cosmetic cream, a beauty essence, a face washing cream, a pack, a cleansing cream and a massaging cream.

5. The skin preparation according to claim 1, wherein said lamellar structure is a multi-lamellar vesicle.

6. The skin preparation according to claim 1, wherein said one or more fatty acid monoglyceride(s) are monoglyceride(s) of saturated or unsaturated fatty acids having 8 to 18 carbon atoms.

7. The skin preparation according to claim 1, wherein said one or more fatty acid monoglyceride(s) are selected from the group consisting of myristic acid monoglyceride, palmitic acid monoglyceride and stearic acid monoglyceride.

* * * * *